US00PP13689P39

(12) United States Plant Patent
Pieters

(10) Patent No.: US PP13,689 P3
(45) Date of Patent: Apr. 1, 2003

(54) CHRYSANTHEMUM PLANT NAMED 'GEDI ONE TAR'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 09/873,495

(22) Filed: Jun. 4, 2001

(65) Prior Publication Data

US 2002/0188983 P1 Dec. 12, 2002

(51) Int. Cl.[7] ..... A01H 5/00
(52) U.S. Cl. ..... Plt./289
(58) Field of Search ..... Plt./295, 286, 289

(56) References Cited

U.S. PATENT DOCUMENTS

PP9,094 P 3/1995 Fuess
PP10,215 P 1/1998 Pieters

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a decorative type inflorescence, consistent flowering response to short days, blooming consistently after 49 days of short day length, free branching habit, light yellow ray florets, very uniform round growth habit, and a large quantity of blooms per flowering branch.

1 Drawing Sheet

LATIN NAME

*Dendranthema morifolium.*

VARIETY

Figure 1:
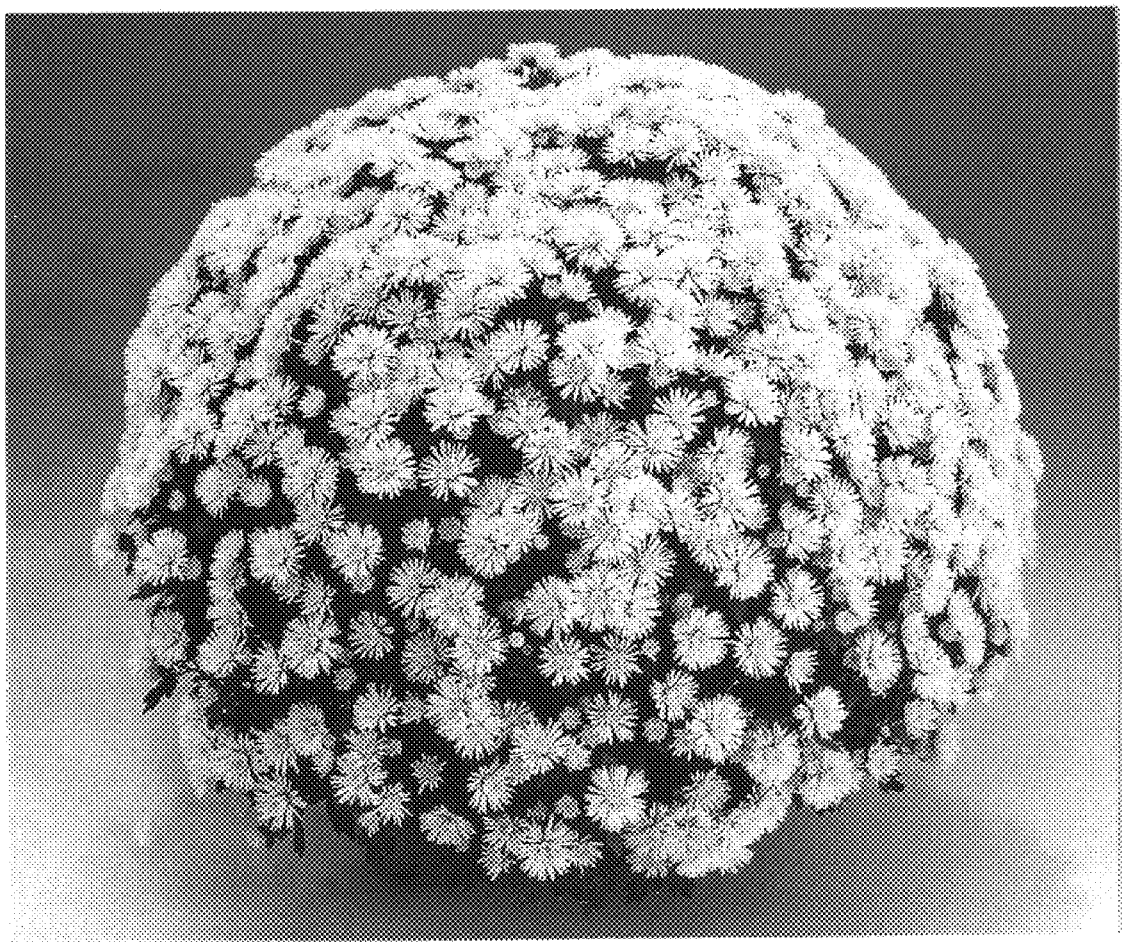

'GEDI ONE TAR'.

BACKGROUND OF THE INVENTION

The present invention relates to a new and distinct cultivar of Chrysanthemum plant, botanically known as *Dendranthema morifolium* and herein after referred to by the cultivar name 'GEDI ONE TAR'.

This new cultivar was the result of hybridization of a female parent, 'Dark Veria' (U.S. Plant Pat. No. 10,215) with a male parent plant of an unpatented Chrysanthemum variety. The new cultivar was selected in October 1997.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'GEDI ONE TAR' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GEDI ONE TAR'. These characteristics in combination distinguish 'GEDI ONE TAR' as a new and distinct Chrysanthemum:

1. Decorative type inflorescence;
2. Consistent flowering response to short days, blooming consistently after 49 days of short day length;
3. Free branching habit;
4. Light yellow ray florets;

5. Very uniform round growth habit; and
6. Large quantity of blooms per flowering branch.

Plants of the new Chrysanthemum are similar to plants of the parent cultivars in most horticultural characteristics, however plants of the new cultivar differ from plants of the female parent cultivar 'Dark Veria' in the following characterictics:

1. The new cultivar has more blooms per flowering branch;
2. The new cultivar naturally blooms 2 weeks earlier;
3. The new cultivar has lighter yellow ray florets; and
4. The new cultivar has a more free branching, round plant habit.

The new cultivar also differed from the male parent in flower type.

The new cultivar can be compared to the Chrysanthemum cultivar 'Citrine' (disclosed in U.S. Plant Pat. No. 9,094). However plants of the new Chrysanthemum differed from the plants of the cultivar 'Citrine' in the following characteristics:

1. The new cultivar has a decorative type flower form;
2. The new cultivar has more ray florets;
3. The new cultivar has a more round plant shape and greater branching; and
4. The new cultivar has more blooms per flowering branch.

BRIEF DESCRIPTION OF THE PHOTOGRAPHS

The photograph shows a plant of 'GEDI ONE TAR' grown in a 2 gallon container. One cutting was used in the pot, planted mid-May and grown under outdoor field conditions.

DETAILED BOTANICAL DESCRIPTION

In the following description, color references are made to The Royal Horticultural Society Colour Chart except where general terms of ordinary dictionary significance are used. The following observations and measurements describe plants grown in a commercial field on Oxnard, Calif. in the month of September 2000. The growing conditions range from 60° to 65° F. at night to 70° to 85° during the day. Measurements and numerical values represent averages of typical flowering types.

Botanical classification: *Dendranthema morifolium* cultivar 'GEDI ONE TAR'.
Commercial classification: Garden-type Chrysanthemum.
Parentage: Hybridization of female parent 'Dark Veria' and male parent (unpatented).

PROPAGATION

Time to rooting: 7 to 14 days at approximately 21° C.
Root description: Fine, fibrous.

PLANT

Growth habit: Mounding herbaceous perennial.
Height: Approximately 22 cm.
Plant spread: Approximately 26 cm.
Growth rate: Moderate.
Branching characteristics: Free branching.
Length of lateral branches: Approximately 18 cm.
Number of leaves per lateral branch: Approximately 24.
Stem color: Near 138A.

FOLIAGE

Leaf:
- *Arrangement.*—Alternate, single.
- *Average length.*—Approximately 6.2 cm.
- *Average width.*—Approximately 3.5 cm.
- *Shape of blade.*—Ovate.
- *Apex.*—Acuminate.
- *Base.*—Attenuate.
- *Attachment.*—Stalked.
- *Margin.*—Pinnately lobed and toothed.
- *Texture of top surface.*—Lightly pubescent.
- *Texture of bottom surface.*—Lightly pubescent.
- *Color.*—Young foliage upper side: Near 137A. Young foliage under side: Near 137B. Mature foliage upper side: Near 137A. Mature foliage under side: Near 137B. Venation upper side: Near 138C. Venation under side: Near 137C.

Petiole:
- *Average length.*—Approximately 2.0 cm.
- *Color.*—Near 137A.

BLOOM

Inflorescence:
- *Flowering habit.*—Induced by darkness period greater than 13.5 hours, approximately 49 days of appropriate day length required to induce and develop blooms.
- *Inflorescence form.*—Quill petal decorative.
- *Natural flowering season.*—Approximately the first two weeks of September.
- *Number of inflorescences per stem.*—Approximately 15.
- *Inflorescence diameter.*—Approximately 5 cm.
- *Inflorescence depth.*—1.5 cm.
- *Inflorescence longevity on plant.*—Approximately 22–26 days.
- *Persistence.*—Persistent.
- *Flower fragrance.*—None.

Ray florets:
- *Appearance.*—Matte.
- *Texture.*—Smooth.
- *Average number per flower.*—Approximately 230.
- *Shape.*—Oblanceolate.
- *Margin.*—Entire.
- *Apex.*—Obtuse.
- *Length.*—Approximately 3.0 cm.
- *Width.*—Approximately 1.0 cm.
- *Color.*—Upper surface at first opening: Near 11A. Upper surface at maturity: Near 11B. Upper surface at fading: Near 11C. Under surface at first opening: Near 12B. Under surface at maturity: Near 12C. Under surface at fading: Near 12D.

Disc florets:
- *Appearance.*—Shiny.
- *Texture.*—Smooth.
- *Average number per flower.*—Approximately 30.
- *Shape.*—Cylindric.
- *Apex.*—Obtuse.
- *Average length.*—Approximately 1 cm.
- *Average width.*—Approximately 0.3 cm.
- *Color.*—At first opening: Near 2A. At maturity: Near 21A. At fading: Near 17D.

Peduncle:
- *Length.*—At terminal end (shortest): Approximately 5 cm. At lateral end (longest): Approximately 9 cm.
- *Texture.*—Smooth.
- *Strength.*—Moderate.
- *Color.*—Near 137C.
- *Habit.*—Erect.

Inflorescence bud:
- *Length.*—Approximately 1 cm.
- *Diameter.*—Approximately 1 cm.
- *Form.*—Globular.
- *Color.*—Near 11A.

Phyllaries:
- *Appearance.*—Matte.
- *Texture.*—Lightly pubescent.
- *Number.*—Approximately 20 to 30.
- *Diameter.*—Approximately 0.4 cm.
- *Length.*—Approximately 0.6 cm.
- *Shape.*—Ovate.
- *Margin.*—Entire.
- *Apex.*—Acute.
- *Color.*—Upper side: Near 137A. Upper side: Near 137A.

Reproductive organs:
- *Ray florets.*—Pistillate: Number of pistils per flower: 1. Stigma shape: 2 branched. Stigma color: Near 16B. Style color: Near 16D. Style length: 0.6 cm.
- *Disc florets.*—Number of pistils per flower: 1. Stigma shape: Cylindric. Style length: Approximately 0.5 cm. Number of stamens per flower: Approximately 5. Anther shape: Tubular. Anther color: Near 16A. Pollen color: Near 17B.

Seed production: Commericially, this plant is not used or observed in a stage wherein seeds would be produced. Therefore, seed production has not been observed to date.

OTHER CHARACTERISTICS

Disease resistance: Neither resistance nor susceptibility observed to date.

What is claimed is:

1. A new and distinct variety of Chrysanthemum plant named 'GEDI ONE TAR' as herein illustrated and described.

* * * * *